(12) United States Patent
Parker et al.

(10) Patent No.: US 6,939,337 B2
(45) Date of Patent: Sep. 6, 2005

(54) MEDICAL DEVICE INCLUDING TUBE HAVING A BRAID AND AN EXPANDED COIL

(75) Inventors: Fred T. Parker, Unionville, IN (US); Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 289 days.

(21) Appl. No.: 09/905,017

(22) Filed: Jul. 13, 2001

(65) Prior Publication Data

US 2002/0032408 A1 Mar. 14, 2002

Related U.S. Application Data

(60) Provisional application No. 60/218,203, filed on Jul. 14, 2000.

(51) Int. Cl.[7] .......................... A61M 25/00; F16L 11/08
(52) U.S. Cl. ...................... 604/528; 604/527; 604/526; 138/124
(58) Field of Search .................... 604/527–528, 604/264, 526, 30, 103.09, 585, 524, 523, 525, 246, 529; 128/831; 138/124, 138; 600/585, 139, 140, 146, 129; 264/526, 138

(56) References Cited

U.S. PATENT DOCUMENTS

| | | |
|---|---|---|
| 4,130,904 A | 12/1978 | Whalen |
| 4,669,172 A | 6/1987 | Petruzzi |
| 4,690,175 A | 9/1987 | Ouchi et al. |
| 4,753,222 A | 6/1988 | Morishita |
| 4,899,787 A | 2/1990 | Ouchi et al. |
| 5,002,041 A | 3/1991 | Chikama |
| 5,005,587 A | 4/1991 | Scott |
| 5,221,270 A | 6/1993 | Parker |
| 5,380,304 A | 1/1995 | Parker |
| 5,462,523 A * | 10/1995 | Samson et al. ............ 604/246 |
| 5,554,139 A | 9/1996 | Okajima |
| 5,573,520 A | 11/1996 | Schwartz et al. |
| 5,700,253 A * | 12/1997 | Parker ........................ 604/526 |
| 5,702,373 A | 12/1997 | Samson |
| 5,769,830 A * | 6/1998 | Parker ........................ 138/124 |
| 5,906,605 A | 5/1999 | Coxum |
| 5,911,715 A | 6/1999 | Berg et al. |
| 5,947,940 A | 9/1999 | Beisel |
| 5,951,929 A | 9/1999 | Wilson |
| 6,053,903 A * | 4/2000 | Samson ....................... 604/523 |
| 6,197,014 B1 | 3/2001 | Samson et al. |

FOREIGN PATENT DOCUMENTS

| | | |
|---|---|---|
| WO | 9315872 | 8/1993 |
| WO | 9964098 | 12/1999 |

* cited by examiner

*Primary Examiner*—Nicholas D. Lucchesi
*Assistant Examiner*—Roz Maiorino
(74) *Attorney, Agent, or Firm*—Brinks Hofer Gilson & Lion

(57) ABSTRACT

A medical device (10) including a tube (11) having a highly uniform and repeatable inner and outer diameter, the tube (11) possessing good trackability, pushability and torquability, and the tube (11) being highly resistant to collapse, necking or kinking during use. The tube (11) first includes a metal coil (14) in a stressed, radially expanded condition, the metal coil (14) preferably being formed as a flat wire. The tube (11) also includes a metal braid (16) extending over at least part of the coil (14). The tube (11) further includes a polymeric bonding layer (18) positioned over and contacting at least the coil (14). The polymeric layer (18) is preferably heat-shrinkable shrinkable tubing made of one or more of nylon or polyurethane. The tube (11) optionally includes an inner liner (20) beneath and in contact with at least part of the coil (14), the liner (20) preferably being composed of PTFE. The polymeric layer (18) maintains the coil (14) in its stressed, radially expanded condition, for example, by adhesion to the coil (14) (such as by thermal bonding to it).

14 Claims, 2 Drawing Sheets

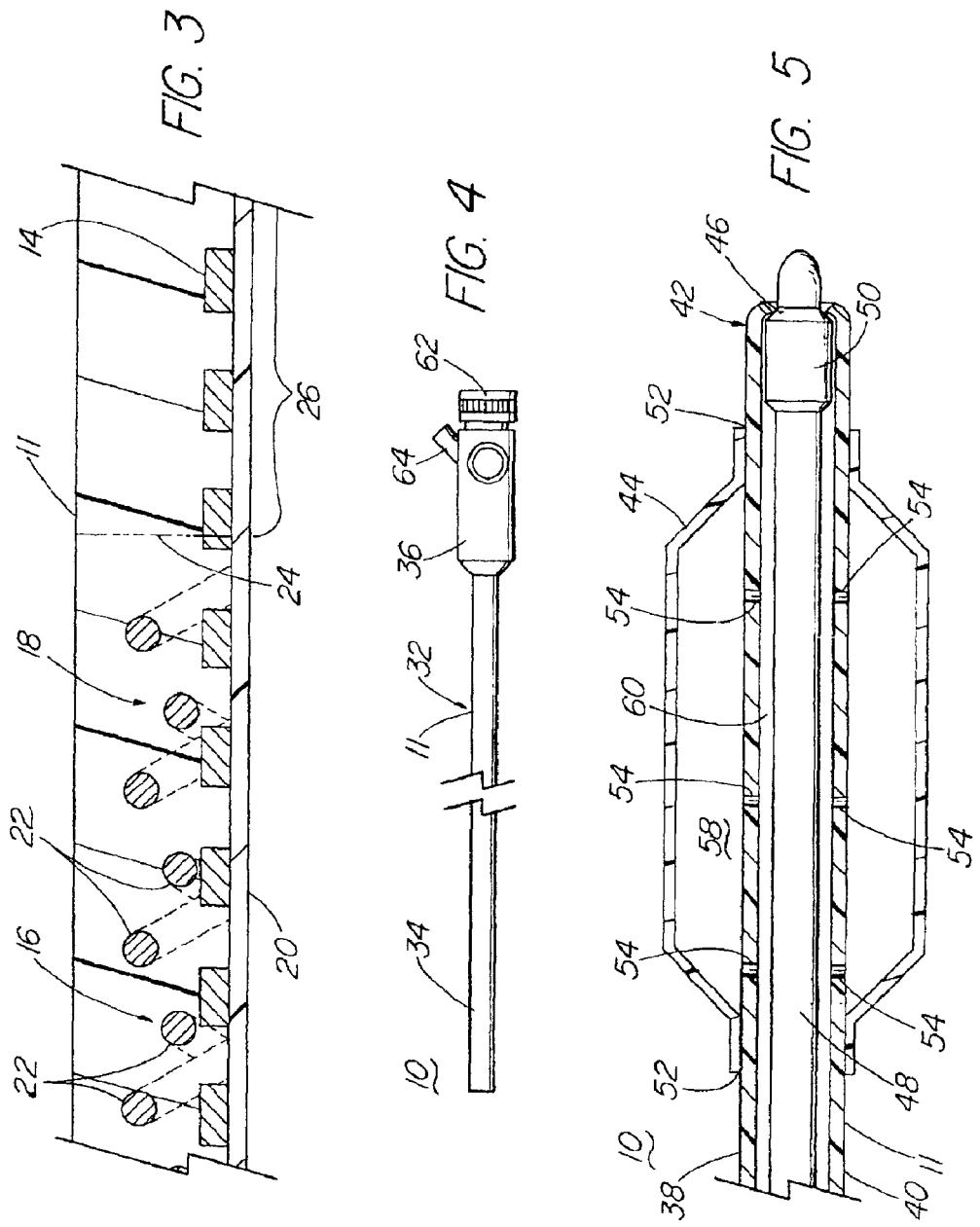

MEDICAL DEVICE INCLUDING TUBE HAVING A BRAID AND AN EXPANDED COIL

RELATED APPLICATION

This application claims priority from U.S. Provisional Application Ser. No. 60/218,203 filed Jul. 14, 2000.

TECHNICAL FIELD

This invention relates generally to medical devices and, more particularly, to devices for expanding a narrowed or obstructed passage or lumen in a patient, or for introducing a medication or catheter therethrough and into a patient, or to a sheath for maintaining access to the vascular system of a patient.

BACKGROUND OF THE INVENTION

Perhaps one of the most important advances in surgery over the last few decades has been the adoption and routine performance of a variety of minimally invasive procedures. Examples of minimally invasive procedures include angioplasty, endoscopy, laparoscopy, arthroscopy and the like. Minimally invasive surgical procedures such as these can be distinguished from conventional open surgical procedures in that access to a site of concern within a patient is achieved through a relatively small incision, into which a tubular device (or tubular portion of a device) is inserted or introduced. The tubular device or device portion (hereinafter, "the tube") keeps the incision open while permitting access to the surgical site via the interior (lumen) of the tube.

The tube can be configured for surgical use itself or can be incorporated into a device which also includes other apparatus having surgical utility. One example of the former is in a balloon catheter, in which the tube is configured (particularly shaped and adapted) as a catheter shaft carrying on it an inflatable balloon. Balloon catheters are useful for performing angioplasty and for the deployment of a stent for preventing stenosis (closure) of a body passage, e.g., a blood vessel. Another example of the former is in a diagnostic, infusion or drainage catheter, in which the tube is configured as a catheter for the delivery of a diagnostic fluid to the patient (for example, for imaging); for the delivery of a therapeutic fluid to the patient (either short or long term); or for the removal of a fluid from the patient. Examples of devices including apparatus in addition to the tube are endoscopes, laparoscopes, arthroscopes or the like, and guide catheters and introducer sheaths (percutaneous or otherwise), through which a guide wire or other surgical device is introduced into the patient.

A variety of tube structures are known to be useful for these purposes. Each of such structures has its own advantages and drawbacks. For example, a balloon catheter is often used in an angioplasty procedure for widening a narrowed site in a blood vessel in a patient. Such a procedure entails advancing the balloon catheter through the tortuous vessels of the vascular system to the narrowed site. During such a procedure, the catheter is torqued, pushed and pulled until the appropriate position is achieved. Further, when the balloon catheter is a single lumen balloon catheter, it may include an occluder within its lumen; the occluder is advanced in the balloon catheter and urged against a valve seat in the distal end of the balloon catheter to seal the catheter and permit inflation of its balloon by introduction of a suitable inflation fluid. Thus, the balloon catheter is also subject during use to a force tending to elongate it, making it particularly subject to undesirable "necking," that is, an undesirable reduction in its outer and/or inner diameter. Of course, necking can arise in other catheter structures and can arise from other causes.

More particularly, to enhance torquability and pushability, some catheters have included a braid in the wall of the shaft of the catheters. Unfortunately, braided catheters are still relatively susceptible to kinking during use. Once a catheter has kinked, fluid cannot pass through the lumen of its shaft. In balloon catheters, this prevents inflation of the catheter balloon. (In other catheters, such as diagnostic, infusion and drainage catheters, prevention of fluid flow similarly interferes with their satisfactory use.) As a result, the balloon catheter must be removed and another catheter introduced into the patient and once again advanced through the vascular system to the narrowed site. This wastes time and increases the potential for trauma to the patient. To prevent kinking, some catheters include a coil in the wall of their shaft, rather than a braid. However, catheters having an embedded coil are undesirably susceptible to necking.

Other medical devices are known which combine a braid and a coil in the wall of a tube incorporated in the devices. For example, a prosthetic blood conduit is known for providing an arterial graft in a patient. The device has a helical reinforcing spring and inner and outer polyester fabric tubes. A variety of known endoscope sheaths have a braid and a coil in the sheath wall, the sheath serving to surround and protect the endoscope itself from bodily fluids during use. One known endoscope sheath is a flexible shaft including a tapered, helical member surrounded by a woven mesh; the mesh and member are purported to give the sheath torsional stability. Another known endoscope tube includes a metallic tubular spiral for resisting collapse and a meshwork tube positioned over the spiral for restricting its longitudinal stretching. Yet another known flexible endoscope tube includes a metal spiral and a fibrous braid fitted over the spiral for elasticity, and for providing the tube with a restoring force that is unhampered by high-polymer materials. Still yet another flexible endoscope tube has two helical coils surrounded by a braid tube, such that the tube will not contract axially during use.

Many of these endoscope tubes share a feature in common: they employ the braid to maintain the coil in a radially compressed condition. Devices other than endoscope tubes are known in which the coil is maintained in a radially expanded condition, for example, the flexible and kink-resistant introducer sheath for percutaneous access disclosed in U.S. Pat. No. 5,700,253 (Fred T. Parker, Dec. 23, 1997) and U.S. Pat. No. 5,380,304 (Fred T. Parker, Jan. 10, 1995), each assigned to Cook Incorporated, Bloomington, Ind. One sheath disclosed in these patents includes a coil positioned between inner and outer tubes. The coil has a diameter less than the outer diameter of the inner tube, the coil being radially expanded and wrapped around an inner tube. The outer tube is then connected to the inner tube through the spaces between the turns of the coil. The patents appear to contain no suggestion to modify the disclosed sheath to further include a braid between the outer tube and the coil. Indeed, it might well be expected that providing such a braid would interfere with the desired connection of the outer tube to the inner tube, defeating the express and intended purpose of the patents.

Many of the other devices disclosed above can be subject to further drawbacks. The successful construction of devices in micro-sizes, having an outer diameter of no more than about 1 or 2 mm, can be problematic. Uniformity of inner and outer diameter along the length of such devices, and uniformity of inner and outer diameter between nominally identical devices, can be difficult to achieve. Moreover, tubes of conventional construction often experience reduced utility if manufactured near such small sizes even if they can be constructed at all. In general, the resulting devices in such small sizes readily collapse, neck and kink during use, and possess poor pushability, poor trackability and poor torquability. Many prior devices do not allow access to sites as deep in the patient than might be desired, or do not allow treatment of structures within the patient as small as might be desired, for example, blood vessels having a diameter on the order of 1 mm. Devices which have a diameter greater than necessary may, of course, be a potential source of trauma to the patient during their use. Devices of such small diameters would be highly desirable because they would allow access to sites deeper in the patient than those sites which can presently be accessed. Such small diameter devices would also be highly desirable because they would permit the treatment of smaller structures within the patient, for example, the expansion of smaller blood vessels than can currently be treated. Smaller diameter devices would also cause less trauma to the patient.

It would be highly advantageous to have medical devices which could readily and reliably be formed with uniform inner and outer diameters, particularly in micro-sizes at or below about 1 mm outer diameter. It would also be highly advantageous to have medical devices, particularly in micro-sizes, which resist collapse, necking and kinking during use. It would further be advantageous to have medical devices, again, particularly in micro-sizes, which possess good pushability, trackability and torquability in use. Finally, it would be advantageous to have such medical devices which enable access to sites deeper within patients than can generally be achieved with devices of conventional construction, and which presented a reduced possibility of trauma to the patient during their use.

SUMMARY OF THE INVENTION

The foregoing problems are solved and a technical advance is achieved in an illustrative medical device for performing any of a variety of minimally invasive medical procedures, including angioplasty, diagnosis, chemotherapy, drainage, endoscopy, laparoscopy, arthroscopy, and the guiding or introduction of other devices into a patient. More particularly, the present invention is directed to a medical device which comprises a tube having a highly uniform and repeatable inner and outer diameter, the tube possessing good trackability, pushability and torquability, and the tube being highly resistant to collapse, necking or kinking during use. The tube first comprises a coil in a stressed, radially expanded condition, and a braid extending over at least part of the coil. The tube further comprises a polymeric bonding layer positioned over and contacting at least the coil. The polymeric layer itself maintains the coil in its stressed, radially expanded condition. The polymeric layer performs this function, for example, by adhesion to the coil (such as by thermally bonding to it). The tube may optionally include an inner liner beneath and in contact with at least part of the coil. However, particularly in smaller diameter constructions, the inner liner is by itself much too weak to prevent the coil from returning to its unstressed, nonexpanded condition. While the polymeric layer has been described as being applied in tubular form over the coil, it could alternatively be extruded over and inside the coil to also form the inner liner 20. The layer 18 and line 20 could add further stability tot he tube. Polymerization could be accomplished in situ.

The tube incorporated in the medical device of the present invention advantageously has an outer diameter no greater than about 2 mm and preferably has an outer diameter no greater than about 1 mm. Medical devices according to the present invention are therefore capable of accessing sites deeper within a patient with decreased potential for trauma to the patient, in comparison to devices incorporating known tube constructions. Exemplary devices which can incorporate the disclosed tube construction include, but are not limited to, balloon catheters (particularly, single lumen balloon catheters); diagnostic, infusion and drainage catheters; endoscopes, laparoscopes and arthroscopes; guide catheters; and introducer sheaths.

Particularly in view of this improved utility, it should be clear that the present invention plainly involves something more than merely providing a braid in the Parker devices disclosed above. Instead of being connected to an inner tube, the polymer layer in the present invention bonds directly to the coil itself; indeed, as indicated above, the inner liner is optional.

In a first aspect, then, the present invention is directed to a medical device comprising a tube, wherein the tube comprises: a coil in a stressed, radially expanded condition; a braid extending over at least part of the coil; and a polymeric layer positioned over and contacting at least the coil; wherein the polymeric layer maintains the coil in its stressed, radially expanded condition. Preferably, the polymeric layer maintains the coil in its stressed, radially expanded condition by adhesion to the coil, for example, by thermal bonding to the coil. The tube advantageously has an outer diameter no greater than about 2 mm, and preferably has an outer diameter no greater than about 1 mm, possibly even as small as about 0.5 mm.

The medical device of the present invention preferably further comprises an inner liner beneath and in contact with at least part of the coil. The inner liner preferably comprises PTFE.

At least one and preferably both of the coil and the braid comprise a medical grade metal. The coil preferably comprises flat wire, while the braid may comprise a plurality of crossed wires that may be of flat or circular cross-section. The polymeric layer preferably comprises at least one of nylon and polyurethane; during manufacture a sleeve of FEP heat-shrinkable tubing (heat fused shrink tubing) may be utilized that is stripped after manufacture. The polymeric layer can comprise two or more discrete longitudinal segments of differing durometer. This provides the resulting tube with differing stiffness at those segments, allowing selection of the flexibility of the tip of the tube. Selective flexibility of the tip of the tube can also be achieved by allowing the coil to extend distally beyond the braid.

As indicated above, the medical device of the present invention can be an endoscope. In such a case, the tube is configured as (that is, particularly structured and adapted for use as) an endoscope sheath. The medical device of the present invention can instead be a single lumen balloon catheter. In this alternative case, the tube is configured as a catheter shaft. More particularly, in this alternative case, the tube preferably has a lumen defined longitudinally through it, and the medical device preferably further comprises an inflatable balloon mounted to the tube, the balloon having an interior in fluid communication with the tube lumen. The tube preferably has a distal end comprising a valve seat, and the medical device preferably further comprises an occluder positioned in the tube lumen and moveable therein, the occluder having a tip engageable with the valve seat of the distal tube end to seal the distal tube end and permit inflation of the balloon (via a suitable fluid source not shown). The lack of stretch and necking of the tube under the force applied by the occluder permits an adequate seal to be established.

In a second aspect, the present invention is directed to a medical device comprising a tube, wherein the tube comprises: a metal coil in a stressed, radially expanded condition, the metal coil comprising flat wire; a metal braid extending over at least part of the coil; a polymeric bonding layer positioned over and contacting at least the coil, wherein the polymeric layer is heat-shrinkable tubing comprising at least one of nylon and polyurethane; and an inner liner beneath and in contact with at least part of the coil, the liner comprising PTFE; wherein the polymeric layer maintains the coil in its stressed, radially expanded condition by adhesion to the coil by thermal bonding to it; and wherein the tube has an outer diameter of up to about 3 Fr (1 mm) or more.

In a third and final aspect, the present invention is directed to the improvement in a medical device including a tube, characterized in that the tube comprises: a coil in a stressed, radially expanded condition; a braid extending over at least part of the coil; and a polymeric layer positioned over and contacting at least the coil; wherein the polymeric layer maintains the coil in its stressed, radially expanded condition.

As indicated above, the medical device of the present invention possesses significant advantages over prior devices. The tube incorporated in medical devices according to the present invention is highly resistant to collapse, necking and kinking during use, and possesses good trackability, pushability and torquability during use. The tube can possess an outer diameter at or below about 1 mm, making it possible for medical devices according to the present invention to access sites deeper within a patient with decreased potential for trauma to the patient. Moreover, the present invention enjoys significant advantages during manufacture, having a highly uniform and repeatable inner and outer diameter even in micro-sizes (at or below about 1 mm outer diameter).

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which:

FIG. 3 is a partial cross-sectional view of another preferred embodiment of the present invention;

FIG. 4 is a side view of another preferred embodiment of the present invention; and FIG. 5 is a partial cross-sectional view of another preferred embodiment of the present invention.

DETAILED DESCRIPTION

Figure 1:
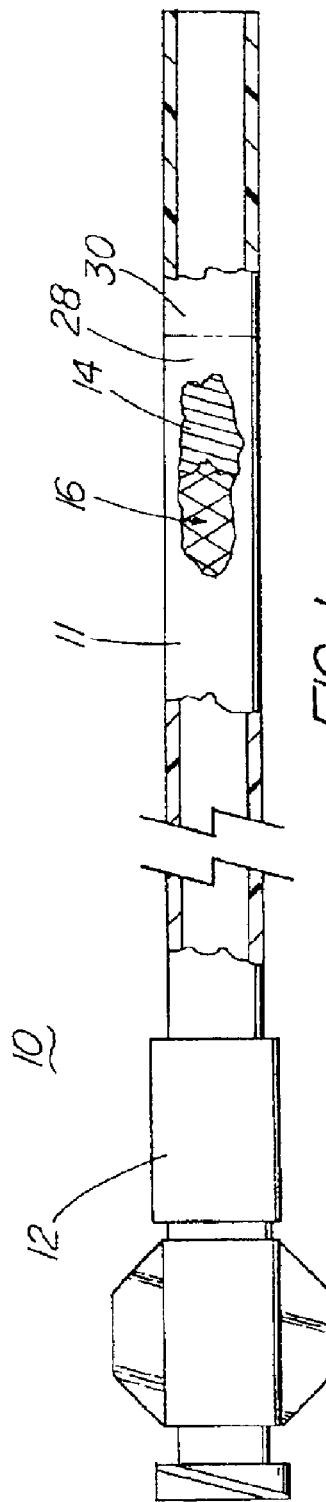
FIG. 1 is a partially cross-sectioned view of the medical device of the preferred embodiment of the present invention.
Figure 2:
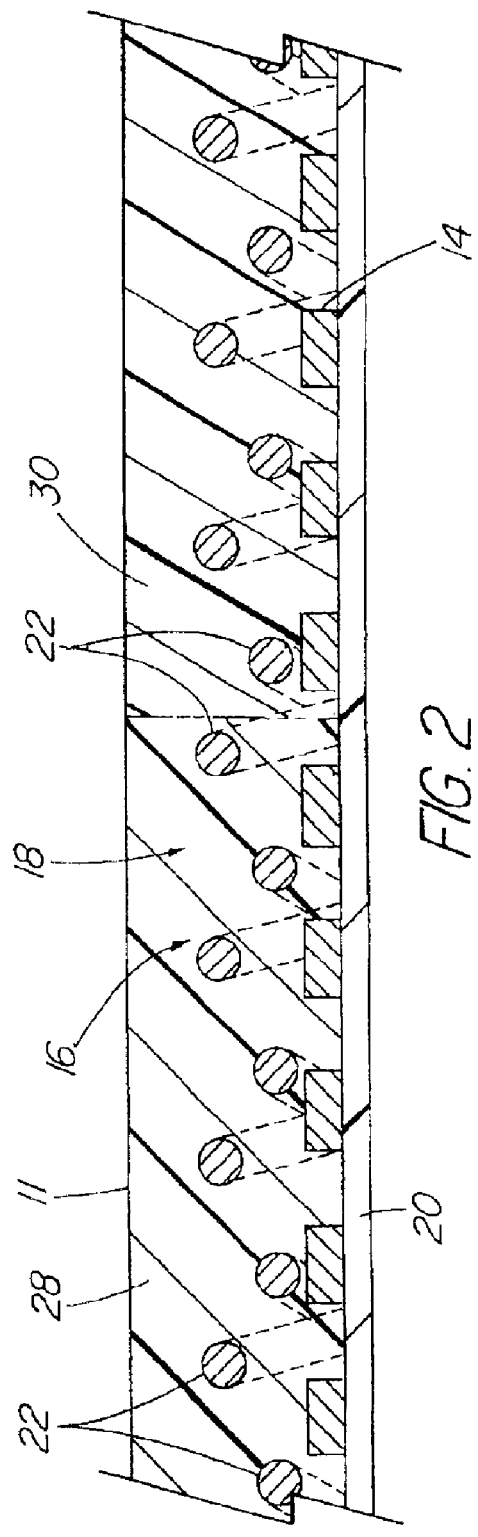
FIG. 2 is a partial cross-sectional view of the medical device of the preferred embodiment of the present invention.

With reference to FIGS. 1 and 2, a first embodiment of a medical device 10 according to the present invention is thereshown, useful for performing any of a variety of minimally invasive medical procedures, including angioplasty, diagnosis, chemotherapy, drainage, endoscopy, laparoscopy, arthroscopy, and the guiding or introduction of other devices into a patient. In its simplest form, the medical device 10 is a simple diagnostic, infusion or drainage catheter 12. The catheter 12 should be considered to also represent a guide catheter or an introducer sheath.

The medical device of the present invention comprises a tube 11. The tube 11 may be up to about 2 to about 3 French (about 0.67 to about 1.00 mm) in outer diameter, and may be as small as about 1.5 French (0.50 mm) or less, in outer diameter. The tube 11 first comprises a coil 14 in a stressed, radially expanded condition. The coil 14 is preferably formed of a flat wire comprised of a medical grade metal. The tube 11 also comprises a braid 16 extending over at least part of the coil 14. The braid 16 preferably comprises a plurality of crossed wires 22 of circular or flat cross-section, and is preferably comprised of a medical grade metal. Other medical grade materials may also be useful for the coil 14 and the braid 16.

The tube 11 further comprises a polymeric bonding layer 18 positioned over and contacting at least the coil 14, and preferably contacting the braid 16 as well. The polymeric layer 18 maintains the coil 14 in its stressed, radially expanded condition. Preferably, the polymeric layer 18 maintains the coil 14 in its stressed, radially expanded condition by adhesion to the coil 14, for example, by thermally bonding to the coil 14. More preferably, the polymeric layer 18 comprises heat-shrinkable (heat fused) tubing. The polymeric layer 18 preferably comprises at least one of nylon or polyurethane.

Any particular portion of the tube 11 can be given a flexibility or springiness which is different from the flexibility or springiness of the remainder of the tube 11. There are several ways in which this difference can be achieved. One way would be to vary the thickness of the polymeric layer 18 along the length of the tube 11; this may not be a particularly practical way to achieve the desired difference. Another way is to permit the polymeric layer 18 to comprise at least two discrete longitudinal segments (such as proximal segment 28 and distal segment 30) of differing durometer. Making the distal segment 30 of the polymeric layer 18 from a softer material than that from which the proximal segment 28 is made yields a tube 11 whose tip is more flexible or springier than the balance of the tube 11. Alternatively, as shown in FIG. 3, the coil 14 may extend distally beyond the distal end 24 of the braid 16. This leaves a distal portion 26 of the coil 14 which is not covered by the braid 16, and similarly yields a tube 11 whose tip is more flexible or springier than the balance of the tube 11.

The tube 11 optionally further comprises an inner liner 20 beneath and in contact with at least part of the coil 14. The inner liner 20 preferably comprises PTFE or another medical grade, lubricious material. Without regard to whether the tube 11 comprises the optional inner liner 20, the tube 11 has a lumen 60 defined in it, which extends longitudinally through it. The lumen 60 can receive a conventional guide wire (not shown) therein, or the lumen 60 can be intended for the delivery of a diagnostic or therapeutic fluid, or the removal of a fluid from the patient.

The stressed coil 14 of the present invention permits the medical device 10 of the present invention to have a wall which is thinner than might conventionally be achieved, and gives the medical device 10 more flexibility and springiness. During use, the tube 11 of the medical device 10 attempts to straighten, making it easier to control advancement of the medical device 10 in the patient. The stressed coil 14 also provides significant advantages during the manufacture of the medical device 10, most notably, better control over the wall thickness ultimately possessed by the medical device 10.

Construction of the tube 11 of the present invention can be straightforward. A mandrel is selected which has a diameter greater than the unstressed, free inner diameter of the coil 14. If employed, the inner liner 20 is placed on the mandrel. The coil 14 is then wrapped about the mandrel (and inner liner 20, if present), the mandrel temporarily maintaining the coil 14 in an expanded condition. The braid 16 is then positioned over the coil 14. Finally, the polymeric layer 18 is established over the braid 16 30 and the coil 14. As indicated above, the polymeric layer 18 is preferably formed from a heat-shrinkable tubing; the mandrel and the elements on it are heated to shrink and cure the polymeric layer 18, and cause it to thermally bond to the coil 14. (The spacing of the braid 16 must be chosen, of course, to allow such bonding or other adhesion to occur.) The mandrel and formed tube 11 are then cooled and the heat reduced sleeve removed, and the tube 11 removed from the mandrel. The polymeric layer 18 now maintains the coil 14 in its stressed, expanded condition.

The tube 11 of the present invention can be put to use in medical devices 10 other than simple catheters. For example, as shown in FIG. 4 the medical device 10 of the present invention can instead be an endoscope 32 of otherwise conventional construction, save for the inclusion of the tube 11. In such a case, the tube 11 is configured as an endoscope sheath 34 connected to a conventional endoscope handle 36, the handle 36 including an ocular tube 62 and a forceps insertion inlet (sidearm) 64.

Alternatively, the medical device 1 0 of the present invention can instead be a single lumen catheter 38 of otherwise conventional construction, again, save for the inclusion of the tube 11. In this case, the tube 11 is configured as a catheter shaft 40, and the medical device 10 then further comprises an inflatable balloon 44 mounted to the tube 11, such that the interior 58 of the balloon 44 is in fluid communication with the lumen 60 of the tube 11. As is conventional, the balloon 44 is preferably secured and sealed to the tube 11 by an adhesive 52. Such fluid communication is established by a plurality of perforations 54 through the tube 11. The perforations 54 can be formed by laser or by cutting with a tungsten cannula.

The tube 11 further has a distal end 42 comprising a valve seat 46, while the medical device 10 further comprises an occluder 48 positioned in the tube lumen 60 and moveable therein. The occluder 48 has an enlarged tip 50 engageable with the valve seat 46 to seal the distal end 42 of the tube 11, thereby permitting inflation of the balloon 44 by pressurized fluid from a source not shown, supplied through the tube lumen 60.

For practical reasons, the tube 11 may not have any special utility in balloon catheters requiring a catheter shaft having two or more lumens. Such balloon catheters might be so large in diameter that they would not enjoy the particular advantages of the tube 11 disclosed herein.

The dimensions (for example, the thickness) of the various elements mentioned above should be selected in view of the purpose of the medical device 10 in which the tube 11 is incorporated. It is believed that the selection of such dimensions will lie within the level of skill in the art of designing surgical instruments, once benefit of the present disclosure is had. While a modest amount of trial-and-error may be needed to obtain optimal dimensions, it is believed that any required experimentation will not be undue. The following may constitute the thicknesses of the various elements of a typical embodiment of the tube 11: inner liner 20, about 0.001 in. (about 0.025 mm) thick, about 0.014 in. (about 0.36 mm) inner diameter; occluder 48 (or guide wire), about 0.010 in. (about 0.25 mm) diameter; wire of coil 14, about 0.0008 to about 0.001 in. (about 0.020 to 0.025 mm) thick; wires 22 of braid 26, about 0.001 in. (about 0.025 mm) in diameter; and polymeric layer 18, about 0.002 in. (about 0.051 mm) thick. The resulting tube 11 would have an outer diameter of about 0.026 in. (about 0.66 mm, or about 2 French).

The present invention can alternatively be considered as an improvement in medical devices 10 including a tube 11. The improvement of the present invention is characterized in that the tube 11 comprises the coil 14 in its stressed, radially expanded condition; the braid 16 extending over at least part of the coil 14; and the polymeric layer 18 positioned over and contacting at least the coil 14. As disclosed above, the polymeric layer 18 maintains the coil 14 in its stressed, radially expanded condition.

The present invention thus provides a medical device 10 which is particularly useful for the performance of a wide variety of catheterization procedures. A medical device 10 including the tube 11 of the present invention can be configured as a balloon catheter (particularly, a single lumen balloon catheter 38); a diagnostic, infusion or drainage catheter 12; an endoscope 32, laparoscope, arthroscope or the like; a guide catheter; or an introducer sheath, among other devices. The present invention is particularly advantageous over prior medical devices in that the tube 11 is highly resistant to collapse, necking and kinking during use and possesses good trackability, pushability and torquability during use. The tube 11 can possess an outer diameter at or below about 1 mm, making it possible for medical devices according to the present invention to access sites deeper within a patient with decreased potential for trauma to the patient. Moreover, the present invention enjoys significant advantages during manufacture, having a highly uniform and repeatable inner and outer diameter even in micro-sizes (at or below about 1 mm outer diameter).

The details of the construction or composition of the various elements of the medical device 10 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure. For practical reasons, however, most embodiments of the medical device 10 of the present invention should probably be considered to be single-use devices, rather than being reusable.

INDUSTRIAL APPLICABILITY

The present invention is useful for a wide variety of catheterization devices and procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A medical device (10) comprising a tube (11), wherein the tube (11) comprises:
   a coil (14) in a stressed, radially expanded condition;
   a braid (16) extending over at least part of the coil (14); and
   a polymeric layer (18) positioned over and contacting at least the coil (14);
   the polymeric layer (18) maintaining the coil (14) in the stressed, radially expanded condition.

2. The medical device (10) according to claim 1, wherein the polymeric layer (18) maintains the coil (14) in the stressed, radially expanded condition by adhesion to the coil (14).

3. The medical device (10) according to claim 1, further comprising an inner liner (20) beneath and in contact with at least part of the coil (14).

4. The medical device (10) according to claim 1, wherein at least one of the coil (14) and the braid (16) comprises a metal.

5. The medical device (10) according to claim 1, wherein the braid (16) comprises a plurality of crossed wires (22).

6. The medical device (10) according to claim 5, wherein the wires (22) are circular in cross-section.

7. The medical device (10) according to claim 1, wherein the coil (14) comprises flat wire.

8. The medical device (10) according to claim 1, wherein the polymeric layer (18) comprises at least one of nylon, polyurethane and PTFE.

9. The medical device (10) according to claim 8, wherein the polymeric layer (18) is encased within an additional layer of heat-shrinkable tubing.

10. The medical device (10) according to claim 2, wherein the polymeric layer (18) is thermally bonded to the coil (14).

11. The medical device (10) according to claim 3, wherein the inner liner (20) comprise PTFE.

12. The medical device (10) according to claim 1, wherein the tube (11) has an outer diameter no greater than about 2 mm.

13. The medical device (10) according to claim 1, wherein the polymeric layer (18) comprises at least two discrete longitudinal segments (28 and 30) of differing durometer.

14. A medical device (10) comprising a tube (11), wherein the tube (11) comprises:
   a metal coil (14) in a stressed, radially expanded condition, the metal coil (14) comprising flat wire:
   a metal braid (16) extending over at least part of the coil (14);
   a substantially imperforate polymeric bonding layer (18) positioned over and contacting at least the coil (14), wherein the polymeric layer (18) is heat shrinkable tubing comprising at least one of nylon, polyurethane and PTFE; and
   an inner liner (20) beneath and in contact with at least part of the coil (14), the liner (20) comprising PTFE;
   wherein the polymeric layer (18) maintains the coil (14) in the stressed, radially expanded condition by adhesion to the coil (14) by thermal bonding to it; and
   wherein the tube (11) has an outer diameter no greater than about 1 mm.

* * * * *